United States Patent [19]

Andresen

[11] 4,110,564
[45] Aug. 29, 1978

[54] TIME-COMPRESSION SYSTEM

[75] Inventor: Richard Paul Andresen, Arlington, Mass.

[73] Assignee: American Optical Corporation, Southbridge, Mass.

[21] Appl. No.: 679,963

[22] Filed: Apr. 26, 1976

[51] Int. Cl.² .......................... G06F 3/14; G11B 5/44; H04N 1/22
[52] U.S. Cl. ...................... 179/15.55 T; 340/324 AD
[58] Field of Search .......... 179/15.55 T, 1 SP, 1 MN; 360/72; 178/DIG. 3; 340/324 AD; 315/394

[56] References Cited

U.S. PATENT DOCUMENTS

| | | | |
|---|---|---|---|
| 3,274,341 | 9/1966 | Allen | 179/15.55 T |
| 3,278,907 | 10/1966 | Barry | 179/15.55 T |
| 3,504,352 | 3/1970 | Stromswold et al. | 179/15.55 T |
| 3,585,440 | 6/1971 | Lee et al. | 340/324 AD |
| 3,763,328 | 10/1973 | Lester et al. | 179/15.55 T |
| 3,786,476 | 1/1974 | Graves | 340/324 A |
| 3,793,626 | 2/1974 | Zambuto | 340/324 A |
| 3,878,560 | 4/1975 | Ramage | 360/72 |
| 3,959,597 | 5/1976 | Keiser | 179/15.55 T |

*Primary Examiner*—Thomas W. Brown
*Assistant Examiner*—E. S. Kemeny
*Attorney, Agent, or Firm*—Jeremiah J. Duggan; Stephen A. Schneeberger

[57] ABSTRACT

A system for the cyclical time-compression of a continuous physiologic waveform provides scan-type display without loss of data during retrace by recording original data at one rate during a retrace-trace cycle, and read-out at a faster rate during the trace period for the compressed display. A feature of the system is use of a single random-access memory which has only the relatively small capacity for storing the data entered from the beginning of the retrace in a time compression cycle until readout at trace period in that cycle begins.

9 Claims, 11 Drawing Figures

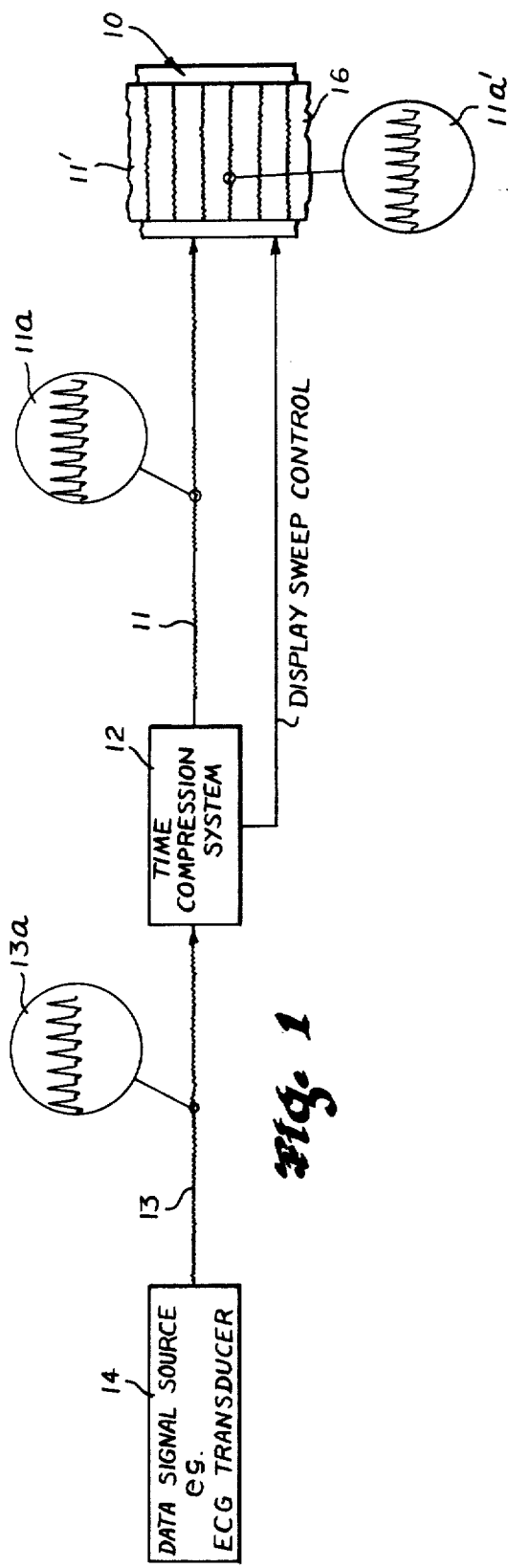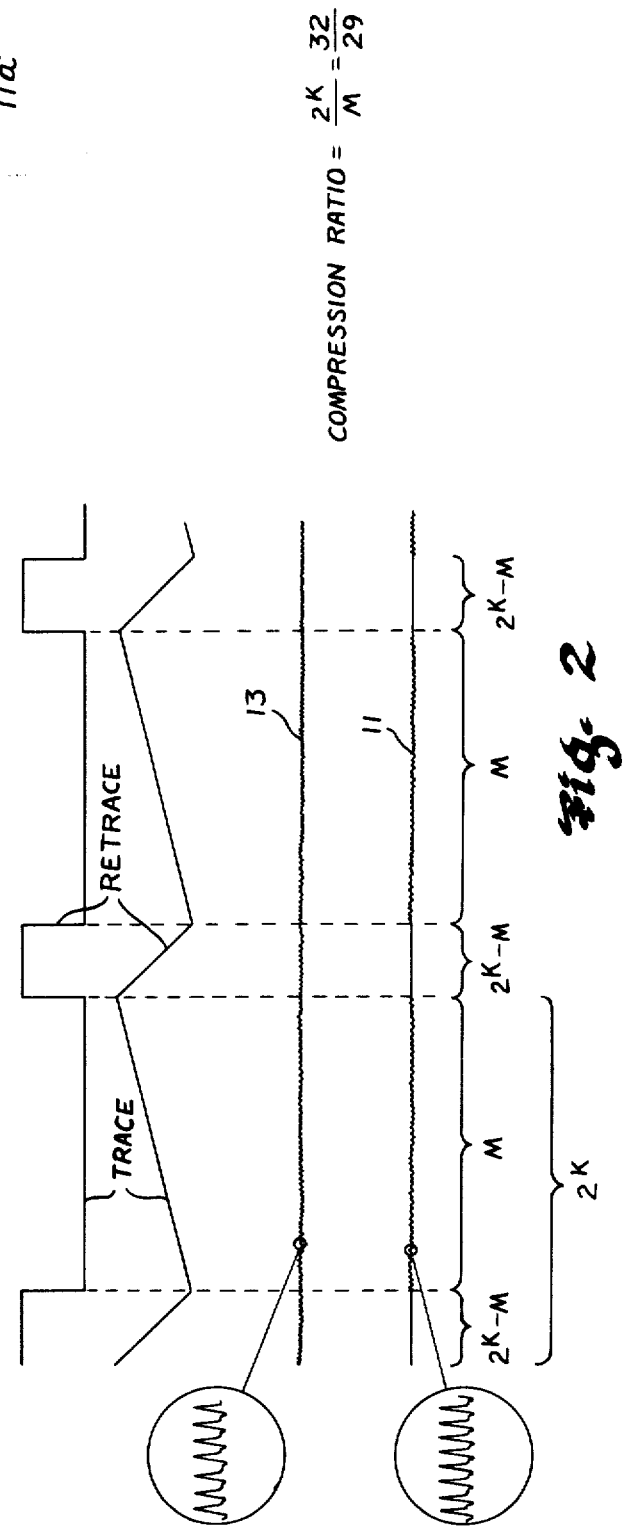

TIME-COMPRESSION SYSTEM

This invention relates to data processing systems, and more particularly to signal waveform display systems. More specifically still, the invention relates to signal waveform time-compression systems.

While the invention relates to data processing systems generally, it is particularly applicable to the display of physiological waveform data from patients, as in electrocardiography and the like. Typically, such waveforms have been recorded by means of continuous-trace strip chart recorders which, while providing a record of excellent quality, generate large amounts of paper which do not lend themselves to incorporation into the patient's records.

A flat-page chart or wide strip chart with the waveform written in a raster-type format may be more convenient from the standpoint of record storage and waveform comparison. Recorders capable of permanently recording the waveform in a raster-type format such as is used with cathode ray tubes, are known. When using such raster format display media, the information or waveform to be displayed is normally continuous and comprises a continuous input to the chart recorder. The information applied to the input of the display device during the ¢trace" phase of each trace-retrace cycle of the raster format is written or traced out, however, the information appearing at the input during the "retrace" phase of the display cycle is "blanked", or not written, and is normally lost.

Even in certain display systems which do not utilize a trace-retrace type raster, as for instance the helical scan recorder described in U.S. Pat. No. 3,893,453 entitled COMPRESSED DATA DISPLAY SYSTEM issued on July 8, 1975 in the name of Goldberg et al. and assigned to American Optical Corporation, the Assignee of the present invention, it may be desirable to periodically interrupt the waveform input signals to the display to create a blank zone or margin for the entry or display of other data. As used hereinafter, the term "retrace" is intended to apply similarly to the "blank" phase or interval in equipment of the type in the immediately aforementioned example.

While in some instances the loss of information occurring during the retrace or signal blanking period may be tolerable, this is not normally so in display systems for waveforms containing physiological information of a patient. In these latter display systems as well as others, it is desirable to retain and display all of the information received from the data source. The retrace portion of a display raster may comprise as much as 10 percent or more of each trace-retrace cycle and thus, the amount of information which may be lost during "retrace" may be significant.

If a display system utilizing a trace-retrace or trace-blank cyclical format is to be employed and all of the continuously available waveform data is to be displayed, the waveform processing system must be capable of storing data during the retrace or blank phase of each display cycle. If the system is operating in real time and data is stored during each retrace period for subsequent write out during a trace period, there remains the problem that new data must also be written out during the trace period. If that new data is itself stored until the previously stored data is routinely read out, it is evident that there will be an increasing, and ultimately excessive, amount of data for storage in successive cycles. Even if the system is not operating in real time, continuous input to the waveform processing system is desired due to the complexities of otherwise stopping and starting a tape or similar off-line storage device for the retrace portion of each display cycle.

In U.S. application Ser. No. 680,017 entitled DATA SEQUENCE DISPLAY SYSTEM AND TIME-COMPRESSION SYSTEM THEREFOR and filed Apr. 26, 1976 by Robert L. Cannon and Christopher C. Day and assigned to American Optical Corporation, the Assignee of the present invention, there is described a system for the time-compression of the source signal waveform whereby the signal appearing at the input to the display means during each trace phase of its display cycle represents in its entirety the source waveform occurring not only during the trace phase, but also during the immediately preceding retrace or blank phase. With this system, the source waveform appears in its entirety in successive traces, albeit in time-compressed form.

In the aforementioned application, periodic samples of the source waveform are sequentially entered in a fixed access, recirculating memory (shift register) at a rate which results in apparent precession of the samples in the memory. When the memory is "full", the samples are read out of memory at a syncopated rate which, on average, is faster than the rate at which samples had entered and are continuing to enter, thereby decreasing the storage delay between entry and readout. However, because a fixed access recirculating shift register is employed, the time-compression ratio is effectively limited to $(n+1/n)$, where $n$ is an integer representative of the length of the trace phase of a trace-retrace display cycle. Further, means are required for equalizing the timing of the data samples being read out of memory at a syncopated rate in order to avoid the distortion in the output waveform which would otherwise result.

Accordingly, it is an object of the invention to provide a system for the time-compression of a continuous data sequence which is of relatively simple, inexpensive and/or efficient design.

It is a further object of the invention to provide a data sequence time-compression system which does not require additional equalization of the timing of data samples read out of storage.

It is an even further object of the invention to provide a data sequence time-compression system having increased flexibility in the selection of time-compression ratios.

SUMMARY OF THE INVENTION

In accordance with the principles of the invention, there is provided a system for the cyclical time-compression of a continuous data sequence which continuously receives and temporarily stores data, as from a waveform, during the trace and retrace phases of a processing or display cycle, and which subsequently reads out substantially all of the stored data in a time-compressed form during the trace phase of the cycle. The rate at which data is read out of storage is uniform and faster than the rate at which it is entered into storage. Further, the compression ratio of the system is fully flexible, though from the standpoint of design convenience at least one of the integers of the ratio may be binary based.

In a particular embodiment of the invention, the data storage is provided by a random access memory capable of storing the requisite number of data samples occurring during the retrace or blanked phase of a display cycle. Separate read and write address counters are indexed at respective different rates such that the ratio of their rates corresponds with the desired compression ratio. The read address counter is inhibited during the retrace or blanked phase of the display cycle while the random access memory is "filled" with incoming data samples. The inhibit signal may also synchronize or otherwise control generation of the sweep signal for a display device.

Further objects, feature and advantages of the invention will become apparent upon consideration of the following detailed description in conjunction with the drawing, in which:

FIG. 1 is a functional block diagram of a waveform display system incorporating the time-compression system of the invention;

FIG. 2 depicts several waveforms which will be helpful in understanding the concept and operation of the time-compression system;

FIG. 5b depicts an expanded portion of the timing diagram of FIG. 5a.

Figure 3:
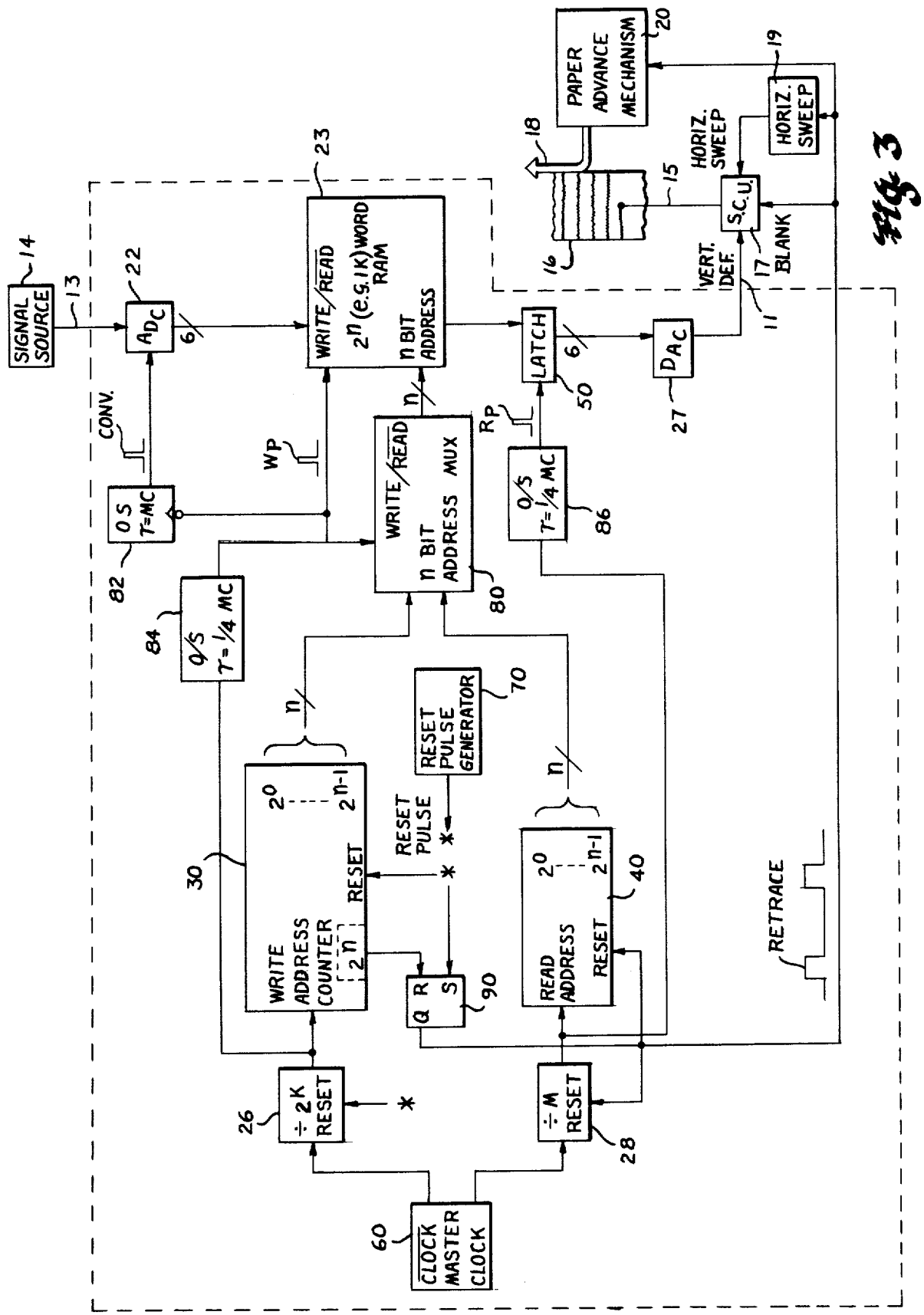
FIG. 3 is a more detailed block diagram of the display system of FIG. 1 showing the novel time-compression system of the invention in greater detail.

In addition to the following description, a further understanding of the invention may be obtained from the description in the aforementioned U.S. application Ser. No. 680,017 of Cannon and Day which is incorporated herein to the extent consistent herewith.

The system of FIG. 1 herein includes a cyclically operating display device, such as the chart recorder 10, for receiving and displaying a signal waveform (11, 11') in time-compressed form from novel time-compression system 12 which receives a real-time based signal waveform 13 from a data signal source 14. The real-time based signal waveform 13 in the illustrative embodiment is a continuous analog ECG waveform and correspondingly, signal source 14 may be an ECG transducer, a playback recorder or the like. Alternatively, waveform 13 may be some other waveform, either physiological or non-physiological, requiring display of substantially its full informational content.

The illustrated display recorder 10, seen in greater detail in FIG. 3, is of a type in which a stylus 15 permanently records input information on a chart 16 adapted to move in incremental steps relative to recorder 10 and stylus 15 in the direction indicated by arrow 18. Stylus control unit 17 operates in a known manner to cyclically move stylus 15 transversely (horizontally in FIGS. 1 & 3) of the direction of movement of chart 16 to provide the horizontal trace and retrace phases of a conventional raster format display cycle.

Horizontal movement of stylus 15 is controlled by horizontal sweep circuit 19 controlled by the RETRACE control signal from time-compression system 12. The RETRACE control signal appears as the uppermost waveform in FIG. 2 and synchronizes the operation of sweep circuit 19. Horizontal sweep circuit 19 applies a control signal such as the sawtooth waveform of FIG. 2, to the stylus control unit 17, the direction and slope of that control signal being indicative of the direction and speed which control unit 17 moves the stylus 15 across chart 16. This sawtooth waveform and its function are the same as that of the horizontal sweep sawtooth in a cathode ray tube display. It will be appreciated that the control signal from sweep circuit 19 might assume a different form, such as the RETRACE signal itself, if the stylus control unit 17 includes a 2-speed bidirectional motor for horizontal movement of the stylus. Further still, the sweep for recorder 10 might be generated independently of timecompression system 12, as with a synchronous motor for the helical scan recorder of the aforementioned U.S. Pat. No. 3,893,453, in which case a sync signal originating at the recorder might be extended to the time-compression system to synchronize it with the recorder each sweep cycle.

Following each trace sweep of stylus 15 and during the retrace sweep phase, chart 16 is stepped by the chart advance mechanism 10 which is actuated by each positive transistion of the RETRACE control signal. It will be appreciated, however, that a chart advancing mechanism providing continuous advance of chart 16 might alternatively be provided, in which case the time-compressed written waveform 11' appearing on chart 16 has a slight downward slope to the right. During the retrace phase of each horizontal sweep, a blanking signal provided by the RETRACE control signal from time-compression system 12 is applied to the stylus 15 through control unit 17 and operates to blank the stylus output during the time of retrace. If the recorder is of the type described in the aforementioned U.S. Pat. No. 3,893,453, a different data signal might be applied to the vertical deflection input of control unit 17 during the so called "retrace" phase and the blanking signal would be omitted.

The relative timing of the trace and retrace phases of the horizontal sweep of stylus 15 is controlled by the RETRACE control signal from time-compression system 12 in which the trace phase, for the purpose of illustration, is 29/32 of the full sweep cycle and the remaining 3/32 comprises the retrace phase. In this illustrative embodiment, it will be seen that data from signal source 14 appears at the input of time-compression system 12 throughout 32/32, or all, of the display sweep cycle and must be compressed into a time representative of 29/32 of the sweep cycle; accordingly, the system exhibits a compression ratio of 32/29 or $2^K/M$, where $2^K$ is an integer representative of the full cycle time and M is an integer representative of the trace phase of the display sweep cycle. Similarly the retrace phase of the sweep cycle may be represented as $2^K-M$. It will be appreciated, following a description of the circuitry comprising time-compression system 12, that the selection of trace phase length to full sweep cycle length is flexible, requiring only that the two relative lengths be expressed as integers; however it may be desirable from the standpoint of design convenience for at least one of the integers of the ratio to be a multiple of a binary based counting system. Selection of the 29/32 ratio of the trace phase illustrates not only the flexibility of the present design but is also representative of a feasible system. To facilitate further illustration and discussion of the invention, a full display sweep cycle is assumed to comprise 64 seconds, with 3/32, or 6 seconds, of each cycle being provided for retrace (or similar related functions) and the remaining 58 seconds being provided for the trace of the source data signal as it appears at the output from time-compression system 12 in time-compressed form. These times are only for purposes of illustration, and it will be realized that other constraints such as a standard clock source frequency and/or the standard speed of the stylus sweep drive unit may require other interval lengths, of the same 29/32 and 3/32 ratios or, in fact, a selection of new ratios may be warranted.

Through reference to the expanded portion 13a of waveform 13 and the expanded portion 11a of waveform 11 in FIGS. 1 & 2, both portions being of identical length and actual time, it will be seen that the characteristic PQRST complex of a heartbeat appears seven times in portion 13a, whereas slightly more than eight such complexes appear in portion 11a. This is representative of the 32:29 time-compression of waveform 13 by the time-compression system 12 which enables waveform 13 to appear in its entirely at the output of system 12 during the 58 second trace phase of each 64 second display cycle.

Referring generally to the time-compression system 12 depicted in FIG. 3, analog data from signal source 14 is converted to a multi-bit digital signal or ward by an analog/digital converter 22, and the resulting successive digital data words are respectively entered and temporarily stored in a random access memory (RAM) 23 in accordance with respective WRITE addresses from a WRITE address counter 30. Similarly, the data words stored in memory 23 are subsequently read out therefrom in accordance with respective READ addressing of the memory by a READ address counter 40 (hereinafter RAC) into an interim storage means, such as data latch 50 connected to memory 23 to receive output data therefrom. Data appearing at the output of latch 50 is extended to a digital to analog converter 27 for reconversion to an analog form and extension to the vertical deflextion input of stylus control unit 17. The counters and associated circuitry may be selected from circuitry available in the TTL, CMOS, ECL logic families and/or the like.

A clock generator 60 generages master clock signals which are extended to the inputs of counters 26 and 28 which divide the count of clock 60 by counts of $2^K$ and M, respectively, for indexing the WAC 30 and the RAC 40 respectively. The various counters are periodically reset by a RESET pulse or a RESET level originating with a RESET pulse generator 70. The alternate READ and WRITE addressing of RAM 23 is controlled by multiplexer 80.

Each data sample obtained at A/D converter 22 comprises a multi-bit digital word which appears in parallel on six output lines (vis, a six-bit digitally coded signal, a binary code being suitable). Correspondingly, each sample of the waveform is stored as a six-bit data word in memory 23. Latch 50 and the input to D/A converter 27 are similarly capable of excepting six-bit parallel data words.

Referring now to time-compression system 12 in greater detail, the waveform 13 applied to analog to digital converter 22 is preferably sampled at least about 100 times per second. In the illustrated embodiment the waveform from signal source 14 is sampled about 171 times per second in order that the 1K (1024 words) preferred capacity of random access of memory 23 is fully utilized in the 6 second retrace interval during each sweep cycle. Accordingly, analog waveform 13 is converted to the digitally coded words by timed conversion pulses (CONV) applied to A/D converter 22. The conversion pulses, CONV, result from the division of the master clock by a factor of $2^K$, or 32 in the illustrated embodiment. By choosing 171 samplings of the analog waveform each second, and considering that counter 26 divides the master clock signal by a count of $2^K$ (32 herein), the clock generator 60 generates a master clock signal having a repetition rate of 5.46 KHz. In fact, clock generator 60 generates 2 square waveforms, CLOCK and $\overline{CLOCK}$, which are the inverse of one another. As before noted, a more conventional clock rate may be selected and the actual time intervals would change somewhat, but the $(M/2^K)$ and the $(2K-M)/2^K$ relationships would be preserved.

Entry of data words from A/D converter 22 into random access memory 23 preferably also occur once per conversion of waveform 13 to the digital word samples. Therefore, the output of $2^K$ counter 26 is also used to index the WAC 30 and to generate a WRITE pulse $^WP$ which times the entry of data into memory 23. The WRITE pulse $^WP$ may be on the order of ¼ to ½ clock cycle in duration. In order that the WRITE pulse $^WP$ not occur simultaneously with the conversion of analog data to digital form by A/D converter 22, the A/D conversion is delayed relative to the occurrence of each WRITE pulse $^WP$ by the inclusion of one-shot 82 intermediate the output of counter 26 and the input of A/D converter 22. The conversion is sufficiently short as to be completed prior to the next WRITE pulse $^WP$ with the exception of first WRITE pulse $^WP$ in each display cycle, this timing permits each successive digital sample to be obtained long before the next successive $^WP$ pulse which enters the sample into RAM 23. To avoid loss of the first data word, the RESET pulse may be used to perform the first A/D conversion. The WRITE pulse $^WP$ is applied to the input of one-shot 82 which in turn serves to delay the generation of the output CONV pulse by the period of one clock cycle (T=CLOCK). Because one-shot 82 is being used for the purpose of delay, its output the CONV pulse is assumed to follow the $^WP$ pulse by one clock cycle. The timing of the one-shot 82, as well as the other one-shots be hereinafter discussed may be controlled by clocking means synchronous with the master clock or by R-C time constants.

As mentioned, the output of $2^K$ counter 26 is extended directly to the input of WAC 30 to index the address counter through a full sequence of WRITE addresses appearing at the output thereof. The WAC 30 is an n-stage "up" counter having n binary outputs, $2^0 \ldots 2^{n-1}$, and additionally includes provision for a carry bit, $2^n$. In the illustrated embodiment in which RAM 23 has a 1K word capacity, WAC 30 must be capable of providing 1024 different addresses. Accordingly, n represents the number 10 such that $2^n$ equals 1024. The 10 outputs ($2^0 \ldots 2^{n-1}$) of WAC 30 are extended to ten respective inputs of n-bit digital address multiplexer 80. Multiplexer 80 may be provided by the requisite number of RCA-CD 4019 AND/OR SELECT gates.

Multiplexer 80 has two groups of n (10) inputs; one n input group for the n output lines of WAC 30 and the other n input group for the n output lines from RAC 40 to be hereinafter discussed. The output of multiplexer 80 includes n output lines extended to n respective inputs of RAM 23 for applying a selected n-bit address thereto. The WRITE pulse $^WP$ provided by the output of $2^K$ counter 26, in addition to being extended to the input of one-shot 82, is also extended to the WRITE/READ input of RAM memory 23 and to the WRITE/READ input of multiplexer 80. Multiplexer 80 is operative to normally extend the output from RAC 40 to the address input of RAM 23 and, during application of WRITE pulse $^WP$ to the multiplexer, is operative to extend the output of WAC 30 to the address input of RAM 23. The WRITE pulse $^WP$, at least in so far as its control over the multiplexer 80 is concerned, has a duration of less than one-half clock cycle so as not to interfere with certain READ operations which may occur during the opposite phase of the same clock cycle, as noted below.

The $\overline{CLOCK}$ output of clock generator 60 is applied to the input of counter 26 and the CLOCK output is applied to the input of counter 28 such that READ and WRITE operations occur on respective opposite half cycles of each clock cycle. The counter 28, in accordance with the invention, divides the master clock signal by a count of M (29 herein) representative of the timelength of the trace portion of the sweep cycle relative to the full sweep cycle length represented by the $2^K$ division of counter 26. The output from counter 28 is extended to the input of RAC 40 for indexing that counter through a full sequence of READ addresses appearing at the output thereof. The RAC 40 is like address counter 30 in that it is an $n$ stage "up" counter having n binary outputs, $2^0 \ldots 2^{n-1}$, however it does not provide for the additional carry bit of WAC 30. As mentioned, the $n$ (10) outputs for RAC 40 are extended to $n$ corresponding inputs of multiplexer 80. Except during the occurrence of a WRITE pulse $^WP$, the multiplexer 80 extends the READ address from RAC 40 to the address input of RAM 23.

The output of M counter 28 also provides a READ pulse, $^RP$, which is comparable in duration (i.e. less than one-half CLOCK cycle) to the WRITE pulse $^WP$. The READ pulse $^RP$ is extended from the output of counter 28 to the strobe input of data latch 50 for timing the latching of data words extended thereto from RAM 23.

Because the WAC 30 and RAC 40 may consist of a large number of stages and may introduce some delay between the appearance of a respective indexing pulse at their inputs and a corresponding address change at the output, it may be necessary to delay the application of the WRITE pulse $^WP$ to multiplexer 80 and RAM 23 and READ pulse $^RP$ to the latch 50. Delay elements such as one-shots 84 and 86 are included in the output circuits of counter 26 and 28 respectively to achieve the necessary delays. One-shots 84 and 86 might typically delay WRITE pulse $^WP$ at both multiplexer 80 and RAM 23, and READ pulse $^RP$ at latch 50, by about one-fourth cycle of the master CLOCK relative to the appearance of the respective pulses at the inputs to the respective WRITE and READ address counters 30 and 40.

A reset pulse generator 70 is operative to extend RESET pulses to the RESET inputs of the counter 26 and the WAC 30 and additionally, to the set input (S) of flip flop 90 at the completion of each successive delay sweep cycle to assure initialization and re-synchronization of the RAC 40 and WAC 30. Pulse generator 70 may comprise a timer or counter which generates a RESET pulse at intervals corresponding with the length of a display sweep cycle (96 seconds herein), and which may be timed by a clock or by some physical occurrence commensurate with completion of a display sweep cycle (e.g. the reset circuitry described in the aforementioned U.S. Pat. No. 3,893,453 ). If the recorder sweep is controlled independently of time-compression system 12, as in the example cited above, the synchronization of the time-compression system 12 might then be slaved to a sync signal from the recorder, thereby obviating the need to extend the RETRACE signal to the recorder.

Alternatively, reset pulse generator 70 might comprise an address comparitor having the outputs of WAC 30 and RAC 40 extended thereto for providing a RESET pulse when the addresses of the two counters are the same, as will occur at the completion of each display cycle. It should be noted however that means must be provided to prevent an address comparitor from responding to identical READ and WRITE addresses which would occur at the beginning of the trace interval.

The RESET pulses from pulse generator 70 are extended to the "set" (S) input of flip flop 90 and the Q output from the flip flop provides a logic level gate signal, hereinafter termed RETRACE. The RETRACE signal goes to a logic "one" when flip flop 90 is set by a RESET pulse and returns to a logic "zero" state when the flip flop is reset by a pulse from the $2^n$ carry-bit stage output of WAC 30 applied to the "reset" (R) input of the flip flop. Thus, flip flop 90 is "set" at the completion of one display sweep cycle, which comprises the initiation of the next sweep cycle, and is reset when the WAC 30 completes it first full address sequence and is about to begin the next address sequence such that the RETRACE signal is in the logic one state only during the retrace phase of the display sweep cycle. The RETRACE signal is extended from the output of flip flop 90 to the RESET inputs of M counter 28 and RAC 40 to prevent their operation during the retrace phase of the sweep cycle in which RAM 23 is initially being filled. Counters 28 and 40 are released at the initiation of the trace phase of the sweep cycle. The RETRACE signal from flip flop 90 is also extended externally of time-compression system 12 to the several control circuits associated with recorder 10 to effect the control thereof hereinbefore discussed.

Reference is made now to the operation of time-compression system 12, and particularly to FIGS. 4a –4f, FIG. 5a, and FIG. 5b. The waveform 13 is converted to data words by convert pulses CONV at the same rate as WRITE pulses $^WP$ provided by counter 26 recur. The WAC 30, following initial reset by pulse generator 70, begins indexing in synchronization with the generation of WRITE pulse $^WP$. Similarly, address multiplexer 80 passes the respective WRITE addresses from WAC 30 to the address input of RAM 23 in synchronization with the occurrence of WRITE pulse $^WP$ at the WRITE/-$\overline{READ}$ control input of RAM 23. The RAM 23, which may be an Intel 2102 random access memory, responds to the application of WRITE pulse $^WP$ at its input to write a corresponding data word appearing at its data input into the respective address location then identified by the address appearing at the address input to the memory, as is well known. The successive generation of WRITE pulses $^WP$ and indexing of WRITE addressing of counter 30 is operative to enter 1024 data words into 1024 respective addresses or storage locations within RAM 23 during the retrace phase of a display sweep cycle. In FIGS. 4a–4f each of the storage locations in RAM 23 is identified by a corresponding number.

Figure 5A:
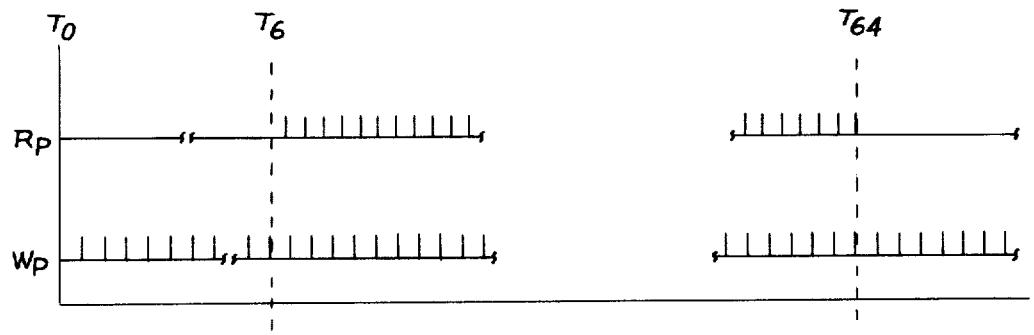
FIG. 5a depicts a timing diagram of the READ and WRITE pulses of the system for a full sweep cycle.

As illustrated in FIG. 5a, only WRITE pulses $^WP$ occur during the first portion of the display cycle to enter 1024 words into memory. At time $^T6$ which is representative of 6 seconds after initiation of the display sweep, WAC 30 will have completed one full address sequence and will generate a carry bit pulse to reset flip flop 90, thereby enabling M counter 28 to begin generating READ pulses $^RP$ and RAC 40 to begin indexing through the READ address sequence.

Figure 5B:
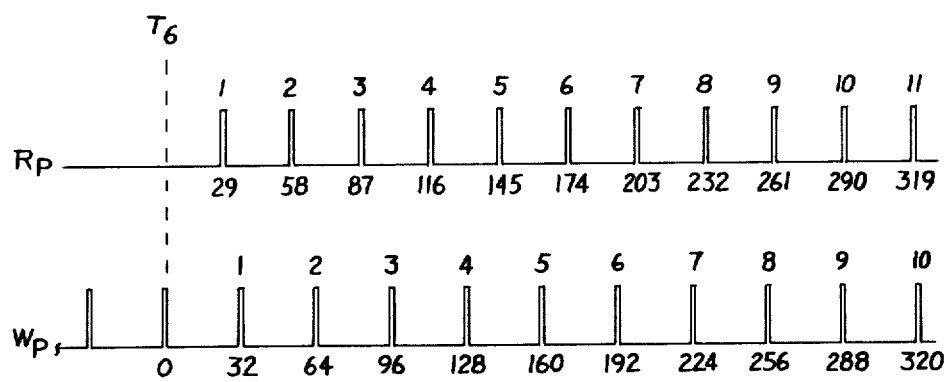

Referring to FIG. 5b, the first READ pulse $^RP$ occurs M (or 29) CLOCK pulses after time $^T6$ and the first WRITE pulse $^WP$ occurs at $2^K$ or (32) $\overline{CLOCK}$ cycles following $^T6$. When this first READ pulse $^RP$ occurs, the storage location in RAM 23 being addressed corresponds with the output of RAC 40, which then is a binary one. The data word stored in that addressed memory location is extended to the data input of latch 50 and the READ pulse $^RP$ strobes its entry into latch 50. The six-bit parallel word output of latch 50 extends to D/A converter 27 whereupon the data word is reconverted to an analog signal amplitude which is extended to the vertical deflection input of stylus control unit 17.

The data word first read out of the "first" address in RAM 23 will have been in storage for the full length of the retrace phase of the display sweep cycle (i.e. 6 seconds). However, the time each successive word entered into RAM 23 during a display sweep cycle remains in storage is successively decreased, as will be hereinafter evident.

The first WRITE pulse $^WP$ (after time $^T6$) is generated three CLOCK cycles after the first READ pulse $^RP$ in correspondence with a binary "one" address from WAC 30 extended to the address input of RAM 23. The data word then appearing at the input to RAM 23 is written into the number "one" storage location in the RAM. In so doing, it writes over the data word previously in that storage location but which has been read out into latch 50 three CLOCK cycles earlier.

Accordingly, 29 clock cycles after the first READ pulse $^RP$, another READ pulse and READ operation will occur. The second WRITE pulse $^WP$ and WRITE operation follow the first WRITE operation by another 32 clock cycles. Thus, it will be seen that because of the difference in the rates of READ pulses $^RP$ and WRITE pulses $^WP$, each successive READ operation associated with a particular memory address is occurring earlier relative to the respective WRITE operation at that address than the proceeding READ/WRITE operation. Stated another way, and with reference to the illustrations of FIGS. 4a-4f, the reading out of information at particular address locations appears to precess in a forward direction relative to the writing of new data words into the respective memory addresses.

Figure 4A:
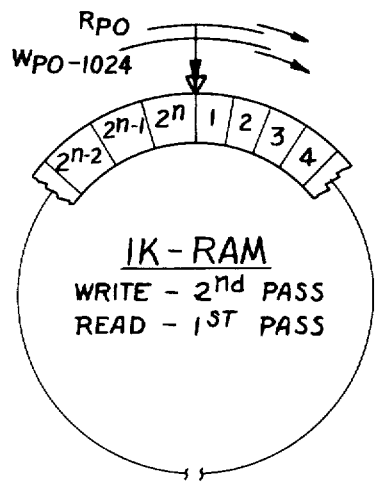
FIGS. 4a–4f depict, in enlarged functionalized form, the precession of the read address relative to the write address throughout a time-compression cycle.
Figure 4B:
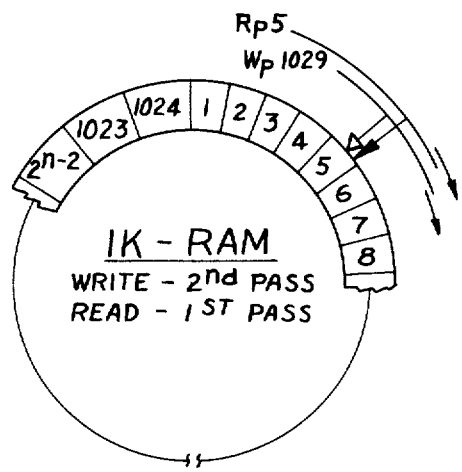
Figure 4C:
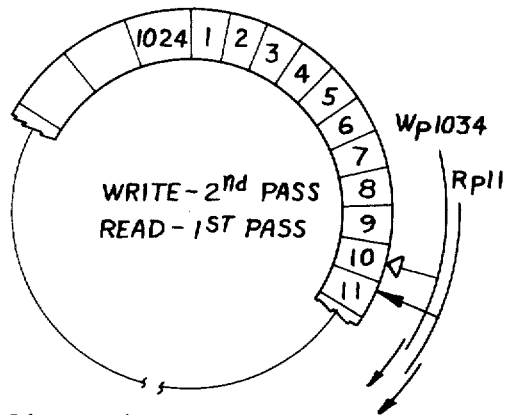
Figure 4D:
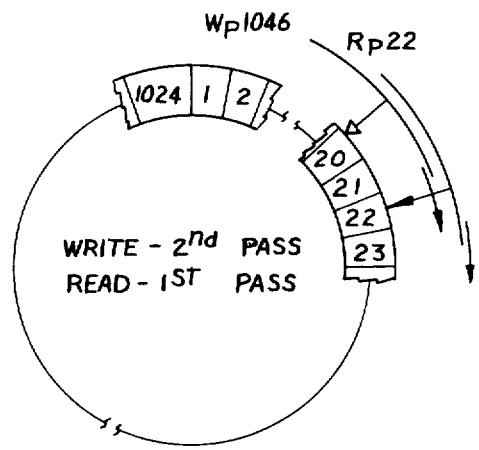
Figure 4E:
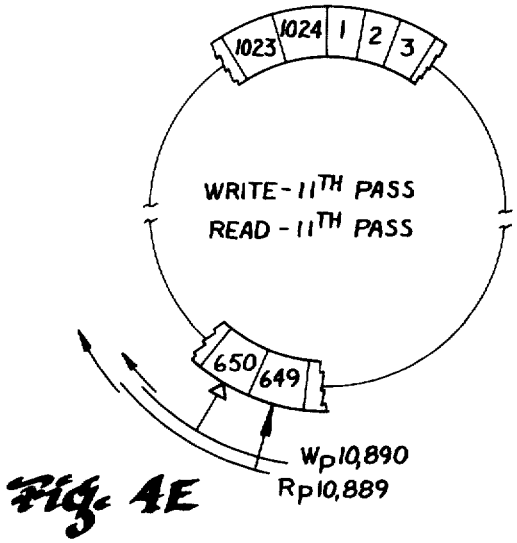
Figure 4F:
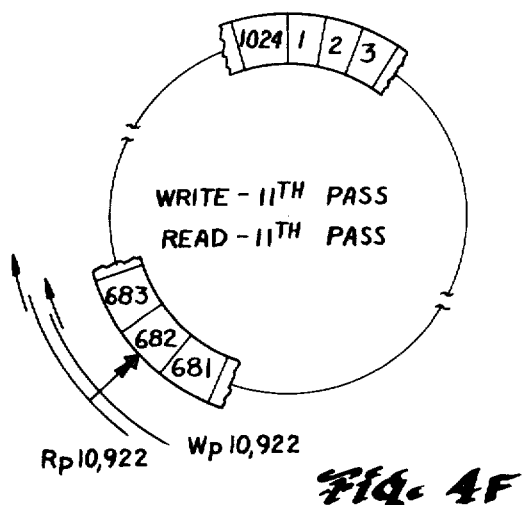

This difference in repetition rates between the READ and WRITE operations results in each successive READ pulse $^RP$ "advancing" in time relative to the subsequently occurring WRITE pulse for the same memory address, the "advance" being such that the READ pulse $^RP$ has forwardly "incremented" one full memory address location relative to the memory address into which a word is presently being written for each interval of 9.66 WRITE pulses $^WP$. Stated another way, the READ operation which interrogates storage location 11 occurs just prior to the WRITE operation which enters a new data word into storage location 10 as illustrated in FIG. 5b. This phenomenon is additionally illustrated in FIG. 4c which shows a READ operation occurring in storage location 11 while a WRITE operation is occurring in storge location 10. (It will be appreciated that the respective READ and WRITE operations do not occur simultaneously because they occur during opposite phases of the clock cycle and may at times be separated by as much as 14 or 15 clock cycles). In FIG. 4b, the READ address is seen to have advanced two storage locations relative to the WRITE address after twenty WRITE operations have occurred (following $^T6$).

This precession of the READ address relative to the WRITE address decreases the time a data word remains in storage and continues until, as illustrated in 4f, the READ operation has advanced by the full length or capacity of the RAM 23, and once again the storge location being read out coincides with that into which a new data word is being written. In effect, the storage delay time of memory 23 is decremented from a maximum to a minimum within the trace phase of each display sweep cycle. Because the incident compression ratio is 32/29 and the memory has a capacity of 1024 words, this "catch-up" will occur at a storage location which is ⅞ through the address sequence of the WAC 30 and RAC 40 (and thus also memory 23) on the eleventh pass therethrough. At this point, the delay-in-storage between entry of a data word and its subsequent readout will have been decremented essentially to zero in coincidence with completion of a respective display sweep cycle. The reset pulse generator 70 then operates to reset the several counters and the sequence is repeated for the next and successive display sweep cycles.

In as much as the data words are being read out of memory 23 at a faster rate then they are entering, the digital word stream extended to D/A converter 27 is time-compressed relative to that appearing at the input to memory 23. Correspondingly, the analog waveform 11 appearing at the output of D/A converter 27 is time-compressed. Further, waveform 11 is essentially undistorted, other than the time-compression, because the rate at which data is read out of RAM 23 is constant.

While digital samples of the input waveform were processed by the time-compression system illustrated, it would be possible with the appropriate analog circuits and memory to process analog samples of the waveform in essentially the same manner, but without A/D and D/A converters.

While a preferred embodiment of the invention has been shown and described, various modifications and substitutions may be made thereto without departing from the spirit and scope of the present invention. Accordingly, it is to be understood that the present invention has been described by way of illustration and not limitation.

We claim:

1. A system for the cyclical timecompression of a signal waveform comprising:

means for periodically sampling the signal waveform to provide sequential waveform data samples;

random access memory means having a predetermined plural number of storage locations, each said storage location storing a respective said data sample for respectively differing periods of time unitl respective readout;

means for entering a plurality of said data samples sequentially into said memory at a first rate throughout a time-compression cycle of predetermined duration; and means for interrogating said memory throughout only a predetermined latter portion of the duration of each time-compression cycle at a second uniform repetition rate having the same ratio to said first rate as the duration of said time-compression cycle has to the duration of said latter portion thereof to read respective said data samples out of memory in the same sequence as entered whereby data samples are read out of memory at a uniform rate faster than said entry rate to substantially represent said waveform in time-compression, said predetermined number of memory storage locations corresponding with the number of said data samples entered in said memory during that former portion of each time-compression cycle which complements said latter portion thereof.

2. The time-compression system of claim 1 wherein said means for entering said data samples into said memory comprise a write address counter for controlling the locations into which said data samples are loaded and means for generating first timing signals for indexing said write address counter and for entry of said data samples into respective memory locations; and said means for interrogating and reading said data samples out of memory comprises a read address counter for controlling the locations in memory from which said data samples are read and means for generating said second timing signals for indexing said read address counter and for read out of said data samples from said respective memory locations.

3. The time-compression system of claim 2 including data latching means and means applying said second timing signals to said data latching means for loading said data samples thereinto during read out from said memory.

4. The time-compression system of claim 2 wherein said means for interrogating said memory only during said latter portion of each time-compression cycle includes means for inhibiting operation of said read address counter during said former portion of each time-compression cycle and for enabling operation of said read address counter during said latter portion of said time-compression cycle.

5. The time-compression system of claim 2 wherein said READ and WRITE address counters are of the same addressing capacity and respectively recycle following full sequential addressing of said plurality of memory storage locations, and including means for initializing said WRITE address counter at the completion of each said time-compression cycle and said READ address counter at the beginning of said latter portion of each said time-compression cycle.

6. The time-compression system of claim 3 wherein said waveform is an analog signal and said time-compression system further includes means for converting said analog signal to digital samples for input to said memory, and means receiving digital samples stored in said latching means for reconversion to an analog signal in time-compressed form.

7. The time-compression system of claim 1 wherein said ratio of the duration of said latter portion of the time-compression cycle to the entire time-compression cycle comprises the ratio of a first integer to a second integer, the difference between said first and second integers being greater than one.

8. A system for the cyclical time-compression of a continuous sequence of data words comprising:

random access memory means having a predetermined plural number of storage locations, each said storage location storing a respective said data word for respectively differing periods of time until respective readout;

means for entering a plurality of said data words sequentially into said memory at a first rate throughout a time-compression cycle of predetermined duration; and means for interrogating said memory throughout only a predetermined latter portion of the duration of each time-compression cycle at a second uniform repetition rate having the same ratio to said first rate as the duration of said time-compression cycle has to the duration of said latter portion thereof to read respective said data words out of memory in the same sequence as entered whereby data words are read out of memory at a uniform rate faster than said entry rate to substantially represent said data sequence in time-compression, said predetermined number of memory storage locations corresponding with the number of said data words entered in said memory during that former portion of each time-compression cycle which complements said latter portion thereof.

9. The time-compression system of claim 1 wherein said cyclical time-compression is repetitive, each successive said time-compression cycle being initiated substantially immediately upon completion of the immediately preceding time-compression cycle whereby entry of said data samples into said memory at said first rate is substantially uninterrupted between successive cycles.

* * * * *